Figure 1:

United States Patent [19]
Persson

[11] Patent Number: 5,380,294
[45] Date of Patent: Jan. 10, 1995

[54] WINDOWED VEIN CATHETER DRESSING

[75] Inventor: Christer Persson, Aneby, Sweden

[73] Assignee: Procter & Gamble Hygien Aktiebolag, Krista, Sweden

[21] Appl. No.: 90,076

[22] PCT Filed: Jan. 24, 1992

[86] PCT No.: PCT/SE92/00030
§ 371 Date: Jul. 20, 1993
§ 102(e) Date: Jul. 20, 1993

[87] PCT Pub. No.: WO92/12757
PCT Pub. Date: Aug. 6, 1992

[30] Foreign Application Priority Data
Jan. 25, 1991 [SE] Sweden ............... 9100230-3

[51] Int. Cl.⁶ ............... A01M 25/02
[52] U.S. Cl. ............... 604/180; 604/177
[58] Field of Search ............... 604/180, 174, 177; 128/DIG. 26

[56] References Cited
U.S. PATENT DOCUMENTS

| | | | |
|---|---|---|---|
| 3,782,378 | 1/1974 | Page | 128/DIG. 26 |
| 3,918,446 | 11/1976 | Buttaravoli | 128/DIG. 26 |
| 4,275,721 | 6/1981 | Olson | 604/180 |
| 4,614,183 | 9/1986 | McCracken | 604/180 |
| 4,633,863 | 1/1987 | Filips | 604/180 |
| 4,669,458 | 6/1987 | Abraham et al. | 128/DIG. 26 |
| 4,704,177 | 11/1987 | Vaillancourt | 128/DIG. 26 |
| 4,838,868 | 6/1989 | Forgar et al. | 604/180 |
| 4,941,882 | 7/1990 | Ward et al. | 604/180 |

FOREIGN PATENT DOCUMENTS

| | | |
|---|---|---|
| 0284219 | 9/1899 | European Pat. Off. . |
| 0168174 | 1/1986 | European Pat. Off. . |
| 0254696 | 1/1988 | European Pat. Off. . |
| 414994 | 9/1980 | Sweden . |
| 419163 | 7/1981 | Sweden . |
| WO90/01351 | 2/1990 | WIPO . |
| WO90/04429 | 5/1990 | WIPO . |

Primary Examiner—Paul J. Hirsch
Attorney, Agent, or Firm—Young & Thompson

[57] ABSTRACT

A vein catheter dressing comprising a supporting foil (1), an adhesive layer (2) on one side of the foil, a liquid-absorbent pad (3) placed centrally on the adhesive layer, the pad being considerably smaller than the supporting foil (1) and being preferably placed within or substantially within one-half of the supporting foil when the foil is divided transversely, and further comprises two release foils (8,9) over the adhesive layer and meeting over or in the vicinity of the pad (3), and a slit (6) which departs from one edge of the dressing and extends substantially up to the pad (3), optionally also through a part of the pad, wherein a window aperture is provided in the supporting foil and optionally also in the adhesive layer (2) in the vicinity of the pad on that side thereof which lies opposite the slit (6), this window aperture being covered with a layer of transparent material (5).

11 Claims, 3 Drawing Sheets

WINDOWED VEIN CATHETER DRESSING

The present invention relates to a vein catheter dressing of the kind described in Patent Specification No. SE-B-414 994 and which includes a supporting foil having on one side thereof an adhesive layer which is covered with a protective, peelable release layer. Located between the adhesive layer and the release layer is a liquid-absorbent suction pad, over which there is suitably placed a non-absorbent liquid-permeable foil. The liquid-absorbent suction pad, or suction layer, is preferably considerably smaller than half the supporting foil and is placed centrally on said foil, especially such that the whole of said suction pad or the major part of said suction pad will lie within one-half of the supporting foil. A slit is provided through the supporting foil, the adhesive layer and the release foil and extends from one edge of the dressing up to the vicinity of the suction pad, so as to form two elongated flaps. When the suction pad is large, and particularly when the suction pad extends towards that edge of the dressing from which the slit begins, the slit may pass through a part of the suction pad, although the imperforate part of the suction pad shall be so large as to effectively cover the place at which the catheter was inserted. The release layer is conveniently divided into two release foils having gripping flaps which meet each other adjacent to or over the suction pad.

The aforedescribed dressing is well known and is well used in medical care establishments. The dressing can be handled, changed and applied easily, without any of the various parts of the dressing sticking to one another, although this will readily occur with an excessively loose slippy dressing or bandage.

Other dressings of similar construction are known to the art, although these known dressings are comprised of transparent plastic material and lack a suction pad. While the aforedescribed vein catheter dressing will keep the wound clean and is satisfactorily firm, while being flexible at the same time, the transparent dressings are extremely slippy and difficult to handle. When the plastic material used is very thin, the dressings become very flimsy, whereas when the thickness of the plastic material is increased, the dressing will not be flexible enough but instead will become comparatively rigid, which renders the dressing unfriendly to the skin and prevents the dressing from accompanying movement of the skin. Furthermore, these known dressings are difficult to remove from the wound, and are easily torn in the process of being removed. The transparent dressings are impermeable to both air and moisture, whereas the vein catheter dressing provided with a suction pad has a supporting foil which is normally made of an air and moisture permeable material and can be made totally or partially impervious or air permeable with the aid of the adhesive layer.

However, blood and fluid may exude from the wound caused by insertion of the catheters. When using the transparent dressing, the fluid will then lie between dressing and skin. When the wound fluid is not absorbed, the fluid will spread so as to obstruct the view through the transparent dressing, while increasing the risk of infection.

The object of the present invention is to provide a vein catheter dressing which possesses the advantages afforded by the dressing which includes a suction pad and a readily-handled supporting foil, while enabling, at the same time, the location at which the catheter is inserted into the vein to be examined or observed visually, without needing to remove the dressing.

The present invention relates to a vein catheter dressing of the kind described in the introduction which, in accordance with the invention, is provided with a transparent window at a location adjacent the suction pad, such that when the dressing is applied the window will lie over the vein location where the catheter was inserted. Thus, merely by glancing at the window it can be seen whether the wound has become infectious or not, while at the same time the insertion is held protected by the pad so that any fluid seeping from the wound will be absorbed thereby.

The inventive vein catheter dressing includes a supporting foil which has an adhesive layer on one side thereof, a liquid absorbent pad placed centrally on the adhesive layer, said pad being considerably smaller than the supporting foil and preferably placed within or generally within one half of the supporting foil when said foil is divided transversely, two protective release foils which extend over the adhesive layer and which meet over the pad or in the vicinity thereof, and a slit which extends from one edge of the dressing to a point which is located substantially adjacent the pad, or alternatively extends through a part of the pad, said dressing being characterized by a window aperture provided in the supporting foil and optionally also in the adhesive layer close to the pad on the side thereof that lies distal from said slit, said window aperture being covered by a piece of transparent material.

The window may have an elongated rectangular shape, a square shape, an oval shape, a circular shape or any other appropriate shape. The window may be completely surrounded by the supporting foil and the pad, or may extend from the pad up to one edge of the supporting foil, so that one edge of the window will form part of the periphery of the dressing. The window aperture may also be extended so that part of the pad, or the whole of said pad, will lie in the window aperture, the pad being secured to the transparent material layer, or alternatively to a part of said layer and a remaining part of the supporting foil. When the layer of transparent material has a large area, the dressing may optionally include a reinforcing edge, made for instance from the same material as the supporting foil, disposed around an outer edge of the window aperture, this outer edge forming part of the edge around the dressing at the same time. The window aperture may also be spaced slightly from the pad, so that a narrow strip of supporting foil will be located between pad and window. Preferably, the window has a generally rectangular or square shape and extends from one edge of the pad up to the nearest edge of the supporting foil. It is particularly preferred that the window has the same width as the pad, although the width of the window may also be smaller or greater than the width of said pad.

The pad may be provided with a recess on that edge which is opposite to the slit and the window aperture may be extended into the recess. The recess may, for instance, have a square or a rectangular shape, or a V-shape or U-shape. The recess is placed over the actual place where the catheter is inserted when applying the dressing. In this case, any fluid which seeps or exudes from the wound will be absorbed by those parts of the pad which lie around the recess, while enabling the insertion wound and the vein to be readily observed at the same time. For the same purpose, the pad may have a slightly smaller extension in a direction opposite to the slit and, when applying the dressing, may be placed precisely at the edge of the insertion wound, so as to both absorb any fluid that seeps from the wound and enable the insertion wound to be examined at the same time.

The window is comprised of an aperture made in the supporting foil and optionally also in the adhesive layer, this aperture being covered by a thin layer of transparent material, such as plastic foil or plastic film. The layer may be given a greater extension than the window aperture, so as to enable the layer to be fastened to the supporting foil and optionally also to the adhesive layer adjacent the aperture. Preferably the side of the transparent layer which faces towards the release foil is also coated with a layer of adhesive. The absence of an adhesive layer will result in poorer adhesion of the dressing to the patients skin and it is more difficult to keep the wound clean in this case. However, adequate adherence can also be achieved with an adhesive layer that is placed around the edge of the window. When the window does not extend up to the edge of the dressing and a part of the supporting foil with adhesive layer thus form the edge of the dressing it is possible to obtain good adherence of the dressing to the skin without any part of the adhesive layer covering the window aperture. The transparent material layer may suitably have the same width as the supporting foil and may extend from the edge of the dressing to a position slightly in beneath the pad, optionally covering the whole surface between pad and adhesive layer. The permeability of the dressing around the catheter insertion point can then be governed through the choice of suitable layer material and layer thickness.

The most suitable dressing embodiment is one in which the window extends from one edge of the pad, optionally including a recess in the pad, up to the edge of the dressing on the opposite side of the slit. The window, however, may be arranged quite separate from the pad, so as to be fully enclosed by the supporting foil, or so as to be enclosed on three sides thereof and to form a part of one edge of the dressing on the fourth side thereof. This latter case enables the vein into which the catheter is inserted to be examined through the window at a position further remote from the catheter insertion point.

The supporting foil is either opaque or semitransparent and is suitably comprised of a woven or non-woven fabric, for instance consisting of polyester, rayon, polypropylene or polyamide. The weight per unit area may be 10-150 g/m$^2$, e.g. 100-150 g/m$^2$, preferably 35-40 g/m$^2$. It is necessary that the material in the adhesive layer is friendly to the skin, e.g. a material based on acrylate. The pad may be made from any well-absorbing, non-toxic material whatsoever, for instance fluff or a fluff-polyester combination. Chip material and purely fiber structures are also conceivable. The liquid-permeable, non-absorbent material, which is optionally placed over the pad, may, for instance, comprise a perforated plastic layer, optionally aluminized, non-absorbent fabric or a permeable, non-absorbent non-woven fabric. The window material may suitably be a thin and pliable film of, e.g. polyurethane, an ether-ester copolymer or an ethylene copolymer, such as ethylenevinyl acetate plastic (E/VAC), ethylene-ethyl acrylate plastic (E/EA), ethylene-butyl acrylate plastic (EBA). The plastics will suitably include an anti-fogging agent. The surface area of the window will be sufficiently large to enable the catheter insertion area to be examined effectively. For instance, the window surface area may be 50-500 mm$^2$, preferably 100-400 mm$^2$, and more preferably 120-180 mm$^2$. The window preferably has the shape of an elongated rectangle and according to one particular embodiment has a size of 12 mm×17.5 mm. When the window extends transversely across the whole of the dressing and surrounds the pad, the window area may be as great as 2000 mm$^2$, or even greater. The layer of window material may be thinner than 40 $\mu$m for instance, and suitably has a thickness of 10-30 $\mu$m, particularly 15-20 $\mu$m.

An exemplifying embodiment of the inventive dressing is illustrated in the accompanying drawings, in which FIG. 1 is a side view of one embodiment of the inventive dressing, provided with release foils; FIGS. 2a-h show the dressing from the adhesive side thereof, with the release foils removed; and FIG. 3 illustrates the dressing from above subsequent to placing the dressing shown in FIG. 2a over a catheter.

The vein catheter dressing shown in FIGS. 1 and 2 includes a supporting foil 1, an adhesive layer 2 which extends over the whole of the supporting foil, an absorbent pad 3 disposed within one-half of the supporting foil 1. The pad may be covered conveniently with a non-absorbent, liquid-permeable layer 4, for instance a thin layer of perforated aluminum foil. A window is cut into the supporting foil and the adhesive layer, and a thin plastic film 5 is arranged in the window aperture thus formed. In the FIG. 2a embodiment, the plastic film 5 extends over the full width of the dressing and slightly in beneath the pad 3 and the supporting foil 1. The plastic film is placed over the adhesive layer 2 and is also covered by an adhesive layer 2. Disposed on the adhesive layer 2 are two release foils 7, 8, each provided with a grip tab. The release foils meet over the pad, or at a position between the pad and a slit 6. When applying the dressing, the release foil 8 which lies over the window and over either a part of the pad 3 or over the whole of said pad is removed first. This part of the dressing is then placed over the catheter, with the pad located over the catheter insertion point and the window located over the extension of the catheter hose, whereafter the other release foil, 7, is pealed off and the legs of the dressing are each placed on a respective side of the catheter housing, so as to secure the housing against the patient's skin.

Figure 2A:
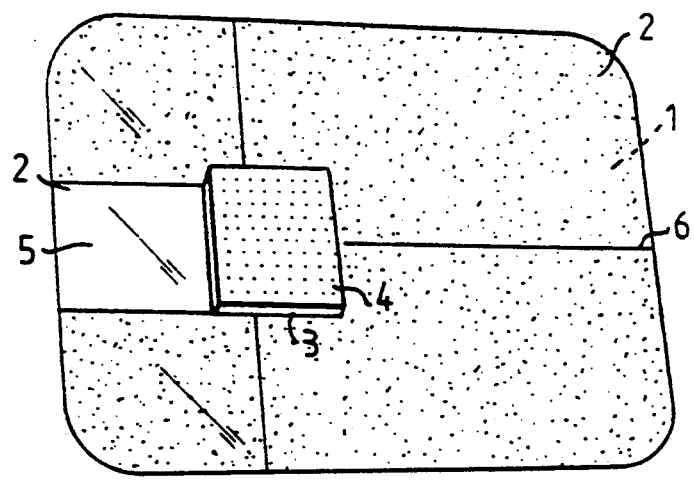
Figure 2C:
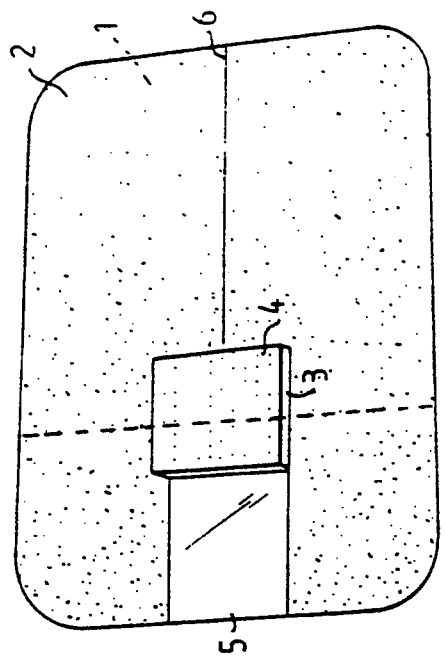
Figure 2E:
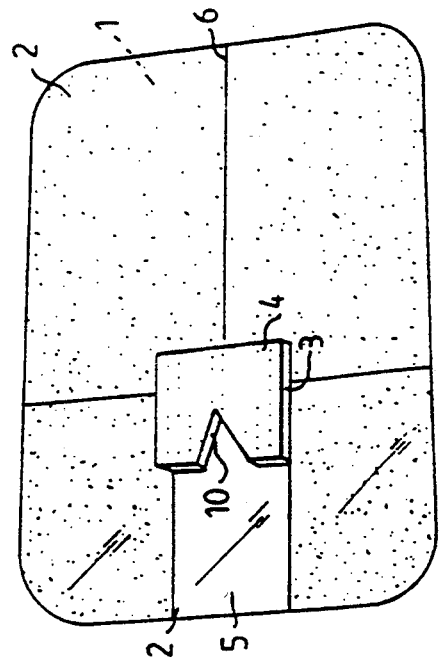
Figure 2B:
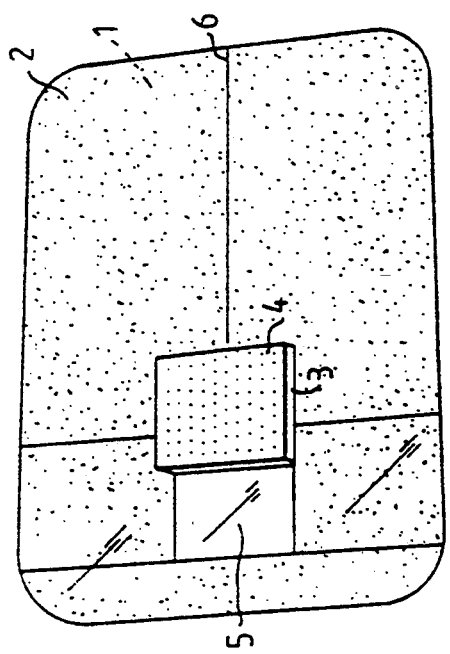
Figure 2D:
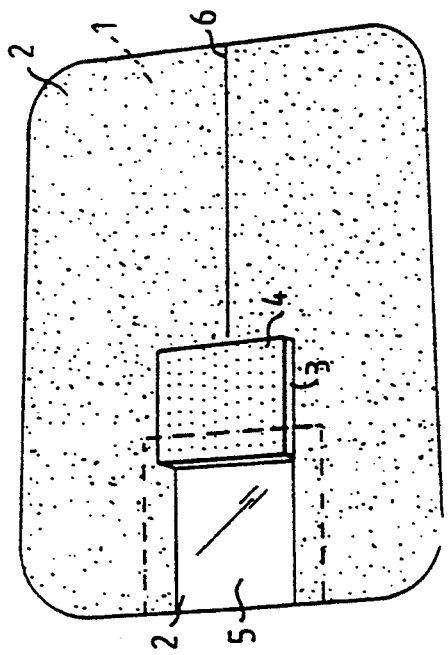

In the FIG. 2b embodiment, the window extends from the pad and terminates slightly short of the edge of the dressing. The window of the FIG. 2c embodiment has the same extension as the window of the FIG. 2a embodiment, although the plastic film is placed on the opposite side of the supporting foil 1. No window aperture is made in the adhesive layer. The plastic film 5 of the FIG. 2d embodiment is also applied to that side of the supporting foil 1 which is opposite to the adhesive layer 2. In this latter case, the plastic film also has a smaller extension than the plastic films of the other embodiments.

Figure 2F:
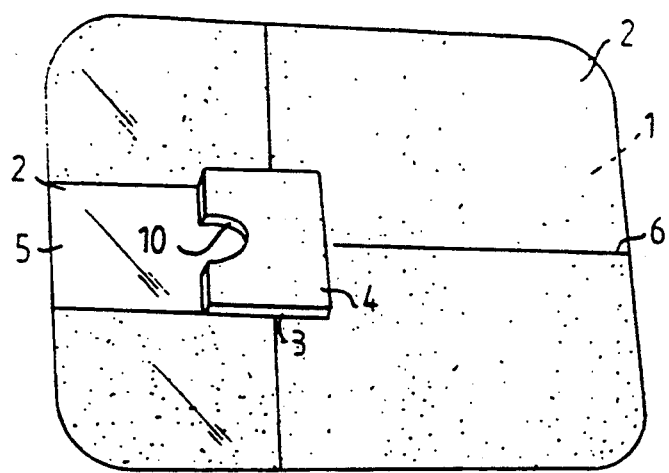
Figure 2G:
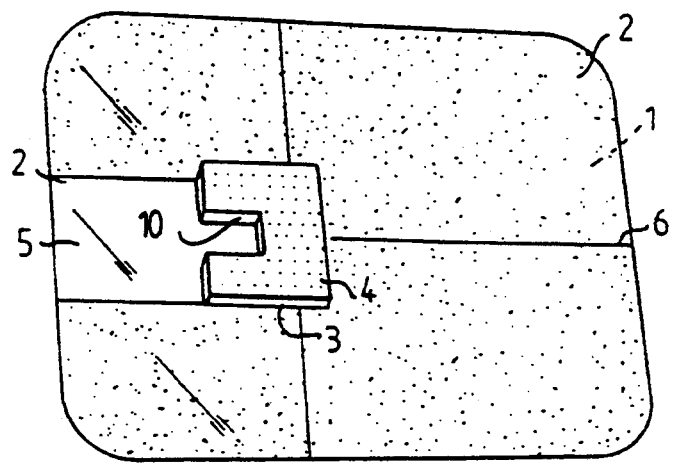

FIGS. 2e-g illustrate three embodiments in which a recess 10 is provided in the pad 3 and the liquid permeable layer 4. The recess 10 of the three embodiments has a V, a U and a rectangular shape respectively. The plastic film 5 has the same form in each of said embodiments and is disposed in the same manner as that illustrated in FIG. 2a. Naturally, the plastic film 5 may also be formed in the manner illustrated in FIGS. 2c and d in the case of embodiments in which a recess is provided in the pad 3, and the window may be formed so that it will not reach the edge of the dressing, as in the case of the FIG. 2b embodiment. In these cases, the film 5 shall, of course, have an extension sufficient to reach beneath the pad 3 and to fully cover the recess 10.

Figure 2H:
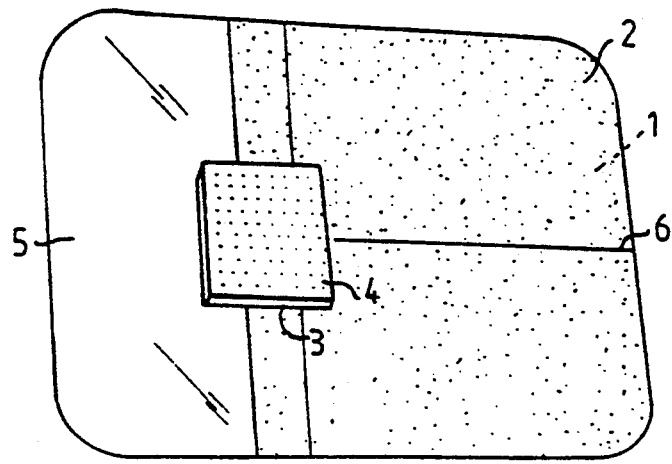

FIG. 2h illustrates an embodiment in which the window aperture forms the whole of the forward part of the dressing. The transparent material layer forms a short side of the dressing and a part of the two long sides. In this case, a strengthening edge may be provided around the outer edge parts of the material layer 5.

Figure 3:
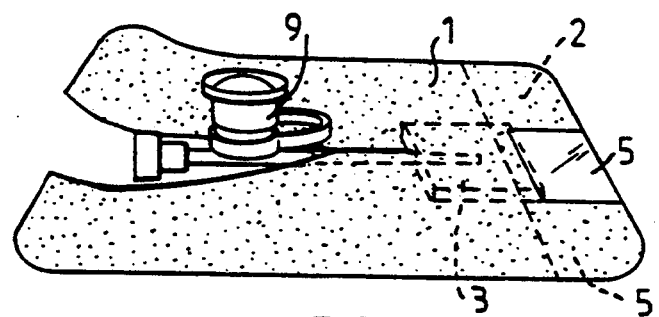

FIG. 3 illustrates the dressing shown in FIG. 2a placed over a vein catheter 9. As will be seen from FIG. 3, the window with the transparent plastic film 5 lies over the vein into which the catheter is inserted, so that any infection spreading through the vein can be seen through the window. When the dressing lacks an absorbent pad or is of the kind illustrated in one of FIGS. 2e-g, the catheter insertion point will also be visible through the window.

I claim:

1. In a vein catheter dressing adapted to secure the housing of a vein catheter on a patient's skin, wherein the dressing comprises a supporting foil (1), an adhesive layer (2) on the side of the foil (1) to be applied to the skin of the patient, a liquid absorbent pad (3) on a central part of said adhesive layer, said pad being adapted to be applied over the incision of the catheter and being substantially smaller than the supporting foil (1) and being spaced inwardly from the margins of the supporting foil, two release foils (7, 8) which before application of the dressing cover the adhesive layer (2) and the pad (3), and a slit that extends in a direction away from the pad through an edge of the dressing; the improvement comprising a window aperture in the supporting foil, said window aperture being disposed on only the side of the pad opposite the slit, and a layer of transparent material (5) covering said window aperture.

2. A window dressing according to claim 1, wherein the pad comprises a non-absorbent liquid permeable foil (4) on the side of the pad opposite the foil.

3. A dressing according to claim 1, wherein the supporting foil is a fabric.

4. A dressing according to claim 1, wherein the transparent material layer has an adhesive layer on the same side thereof as said release foils.

5. A dressing according to claim 1, wherein the pad and supporting foil have a recess on the side of the pad opposite the slit, said transparent material layer also covering said recess.

6. A dressing according to claim 1, wherein the transparent material layer contains an anti-fogging agent.

7. A dressing according to claim 1, wherein the transparent material layer is disposed on the side of said supporting foil which is opposite said adhesive layer.

8. A dressing according to claim 1, wherein the transparent material layer is covered by the adhesive layer.

9. A dressing according to claim 1, wherein the window aperture has about the same width as the pad and extends from the pad up to the nearest edge of the dressing.

10. A dressing according to claim 1, wherein the window aperture extends transversely over the whole of the dressing, from adjacent the pad to an edge of the dressing opposite said slit.

11. A dressing according to claim 1, wherein the window aperture extends from the pad and terminates a short distance from an edge of said dressing in a direction away from said slit.

* * * * *